United States Patent [19]

Chang et al.

[11] Patent Number: 4,681,709
[45] Date of Patent: Jul. 21, 1987

[54] ALKYL 9-ALKOXY-7-NONENOATES

[75] Inventors: Biau-Hung Chang, West Chester; Ronnie M. Hanes, Milford, both of Ohio

[73] Assignee: National Distillers and Chemical Corporation, New York, N.Y.

[21] Appl. No.: 914,903

[22] Filed: Oct. 3, 1986

[51] Int. Cl.$^4$ ............................................. C07C 69/533
[52] U.S. Cl. ................................. 260/410.9; 562/590
[58] Field of Search .................. 260/410.9 Q; 568/689

[56] References Cited

U.S. PATENT DOCUMENTS

| 3,036,100 | 5/1962 | Pfeiffer et al. | 260/410.9 Q |
| 3,112,330 | 11/1963 | Oughton | 260/410.9 Q |
| 3,140,303 | 7/1964 | De La Mare et al. | 260/410.9 Q |
| 3,156,714 | 11/1964 | Surmatis | 260/410.9 Q |
| 3,330,840 | 7/1967 | Pryde et al. | 260/410.9 Q |
| 3,499,042 | 3/1970 | Smutny | 568/690 |
| 3,670,029 | 6/1972 | Romanelli | 568/689 |
| 4,138,418 | 2/1979 | Warning et al. | 560/186 |
| 4,311,862 | 1/1982 | Drent | 568/689 |

FOREIGN PATENT DOCUMENTS 688555  3/1953  United Kingdom ............... 560/186

Primary Examiner—J. E. Evans
Attorney, Agent, or Firm—Kenneth D. Tremain

[57] ABSTRACT

A new class of compounds, the alkyl 9-alkoxy-7-nonenoates, is disclosed. These compounds are important intermediates in the synthesis of sebacic acid.

4 Claims, No Drawings

ALKYL 9-ALKOXY-7-NONENOATES

BACKGROUND OF THE DISCLOSURE

1. Field of the Invention

The present invention is directed to a new class of allylic ethers. More specifically, the present invention is directed to a class of allylic ethers having carboxylate functionality, the alkyl 9-alkoxy-7-nonenoates. 2. Background of the Prior Art Sebacic acid is a commercially important compound having particular application in its ester form as a plasticizer for polymers, especially polyvinyl chloride. This compound is relatively expensive because the only commercial method for its formation relies on a naturally occurring product, castor bean oil. Sebacic acid is obtained from said castor bean oil by extraction and oxidative cleavage. Although sebacic acid is expensive its unique flexibility and volatility properties support continued use of the compound as a plasticizer in polymeric applications. Obviously, the manufacture of this compound by synthetic means would be highly desirable.

It has now been suggested that a nonenoate having ether functionality at the end of the straight chain molecule opposite the ester functionality can be esterified to produce a diester which can be also easily synthesized to sebacic acid by hydrogenation and hydrolysis. The difficulty with this proposal is that a suitable nonenoate is not available in the prior art.

The compound methyl 9-methoxy-8-nonenoate is known in the art. This compound is disclosed in E.H. Pryde et al., Polymer Eng & Sci. 6, 60–65 (1966). Those skilled in the art are aware that this compound is a vinyl ether. The carbonylation reaction of a vinyl ether to form the ester, and thus produce a diester, is very difficult. Such reaction occurs at low rate and low selectivity and must be accompanied by extreme thermodynamic conditions, that is, at very high pressure and temperature. On the other hand, the equivalent carbonylation reaction of an allylic ether occurs at high rate and high selectivity, under moderate thermodynamic conditions, to easily produce the ester, that is, the diester when the starting reactant is an ester.

It is therefore not surprising that 9-methoxy-8-nonenoate, which, in E. H. Pryde et al., J. Org. Chem 29, 2083 (1964), is described as synthesizable from methyl 9,9-dimethoxynonanoate in a cracking reaction, although disclosed to have application as a plasticizer (E. H. Pryde et al., J.A.C.S. Div. of Org. Coatings, Plastics Chem Preprint 23 (2), 144 (1963)), is not suggested as an intermediate in the formation of a dicarboxylic acid.

The above remarks establish the need in the art for a new class of compounds which can be utilized as intermediates in a synthetic process for making sebacic acid.

SUMMARY OF THE INVENTION

A new class of compounds have now been discovered which can easily be carbonylated to yield a class of diesters which are easily synthesized to sebacic acid by hydrogenation and hydrolysis.

In accordance with the instant invention, a new class of allylic ethers, the alkyl 9-alkoxy-7-nonenoates, is disclosed.

DETAILED DESCRIPTION

The present invention is directed to a generic class of compounds denoted as alkyl 9-alkoxy-7-nonenoates. These compounds have the structural formula

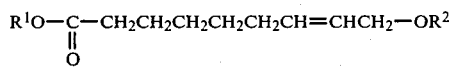

where $R^1$ and $R^2$ are the same or different and are $C_1$–$C_6$ alkyl. More preferably, $R^1$ and $R^2$ are the same or different and are $C_1$–$C_4$ alkyl. Still more preferably, $R^1$ and $R^2$ are the same or different and are $C_1$–$C_2$ alkyl.

Among the compounds within the scope of the present invention are methyl 9-methoxy-7-nonenoate, methyl 9-ethoxy-7-nonenoate, methyl 9-propoxy-7-nonenoate, methyl 9-butoxy-7-nonenoate, methyl 9-pentoxy-7-nonenoate, methyl 9-hexoxy-7-nonenoate, ethyl 9-methoxy-7-nonenoate, ethyl 9-ethoxy-7-nonenoate, ethyl 9-propoxy-7-nonenoate, ethyl 9-butoxy-7-nonenoate, propyl 9-methoxy-7-nonenoate, propyl 9-ethoxy-7-nonenoate, propyl 9-propoxy-7-nonenoate, propyl 9-butoxy-7-nonenoate, butyl 9-methoxy-7-nonenoate, butyl 9-ethoxy-7-nonenoate, butyl 9-propoxy-7-nonenoate, butyl 9-butoxy-7-nonenoate, pentyl 9-methoxy-7-nonenoate, pentyl 9-ethoxy-7-nonenoate, hexyl 9-methoxy-7-nonenoate, hexyl 9-ethoxy-7-nonenoate and the like.

The alkyl 9-alkoxy-7-nonenoates of the present invention find significant utility as an intermediate in the synthesis of sebacic acid. These compounds are easily carbonylated to replace the allylic ether function to yield the diester in a route to the formation of the dicarboxylic acid, sebacic acid, as discussed above.

The compounds of the present invention are formed by reacting an 8-alkoxy-1,6-octadiene with carbon monoxide and an alkanol in the presence of a cobalt catalyst to produce the alkyl 9-alkoxy-7-nonenoate. In a preferred embodiment the cobalt catalyst is a cobalt coordination compound, preferably cobalt carbonyl having the structural formula $Co_2(CO)_8$. The ligand, pyridine is also preferably included in the cobalt coordination compound.

The following example is given to illustrate the present invention. Because this example is given for illustrative purposes only, the invention should not be limited thereto.

EXAMPLE

Preparation of Methyl 9-methoxy-7-nonenoate

A 300 ml. stirred reactor after being purged with nitrogen was charged with 65.0 g. (0.464 mol) 8-methoxy-1,6-octadiene; 29.7 g. (0.927 mols) methanol; and 33.1 g (0.418 mol) pyridine. These liquids had originally been combined in a bottle prior to being charged into the reactor. Separately, 3.17 g. (9.27.mmols) $Co_2(CO)_8$ was added to the stirred reactor. Upon sealing, the reactor was purged three times with carbon monoxide, pressurized to 40 psig with hydrogen and then to 3,500 psig with carbon monoxide. After stirring for a few minutes the reactor was heated to 150° C. and the pressure adjusted to 4,000 psig with carbon monoxide. The reactor was maintained at these conditions for three hours.

Upon reaction completion the product was analyzed by gas chromotography and found to include methyl 9-methoxy-7-nonenoate in a yield of 46.3%.

Methyl 9-methoxy-7-nonenoate was isolated and characterized by spectral data. An infrared spectrum analysis was performed on the neat product with the following results (all measured in cm$^{-1}$): 3,020(m-w), 2,920(s), 2,845 (s-m), 2,810 (m), 1,730(s), 1,660(w), 1,445(m), 1,425(m), 1,350(m-w), 1,245(m), 1,185(s-m), 1,160(s-m), 1,110(s-m) and 960(m).

Note: s=strong, m=medium and w=weak

Nuclear magnetic resonance analysis yielded the following results:

$^1$H-NMR Spectrum (in CDCl$_3$) ($\delta$,ppm)=1.32–1.44 (multiplet,4H); 1.62 (quintet,2H); 2.05 (quartet,2H); 2.30 (triplet,2H); 3.29 (singlet,3H); 3.65 (singlet,3H); 3.84 (doublet,2H); and 5.42–5.78 (multiplet,2H).

$^{13}$C-NMR Spectrum (in CDCl$_3$) (ppm)=24.552, 28.411, 28.520, 31.850, 33.670, 51.038, 57.286, 72.883, 126.174, 133.902 and 173.514.

Mass spectrum (characteristic peaks in m/e) was as follows: 200(M+), 185, 168, 136, 94, 71.

The above preferred embodiments and example are given to illustrate the scope and spirit of the present invention. These embodiments and example will make apparent, to those skilled in the art, other embodiments and examples. These other embodiments and examples are within the contemplation of the present invention. Therefore, the present invention should be limited only by the appended claims.

What is claimed is:

1. A compound having the structural formula

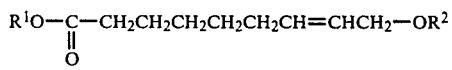

where $R^1$ and $R^2$ are the same or different and are $C_1$–$C_6$ alkyl.

2. A compound in accordance to claim 1 wherein $R^1$ and $R^2$ are the same or different and are $C_1$–$C_4$ alkyl.

3. A compound in accordance with claim 2 wherein $R^1$ and $R^2$ are the same or different and are $C_1$–$C_2$ alkyl.

4. A compound in accordance with claim 3 wherein said compound is methyl 9-methoxy-7-nonenoate.

* * * * *